United States Patent [19]
Ranjekar et al.

[11] Patent Number: 6,037,128
[45] Date of Patent: Mar. 14, 2000

[54] PROCESS FOR THE PREPARATION OF SEMISYNTHETIC AMPLICON USEFUL FOR SEX DETERMINATION OF THE PAPAYA PLANT

[75] Inventors: Prabhakar K. Ranjekar; Anjali S. Parasnis; Vidya S. Gupta, all of Pune, India

[73] Assignee: Council of Scientific & Industrial Research, New Delhi, India

[21] Appl. No.: 09/052,505

[22] Filed: Mar. 31, 1998

[30] Foreign Application Priority Data

Mar. 31, 1997 [IN] India ................................. 268/Del/97
Aug. 28, 1997 [IN] India ................................ 2447/Del/97

[51] Int. Cl.[7] ............................. C12Q 1/68; C12P 19/34; C07H 21/02; C07H 21/04
[52] U.S. Cl. ............................ 435/6; 435/91.2; 435/471; 536/23.1; 536/24.3; 536/24.33; 536/23.6
[58] Field of Search ............................. 435/6, 91.1, 91.2, 435/91.5, 471; 536/23.1, 24.3, 24.33, 23.6

[56] References Cited

U.S. PATENT DOCUMENTS 5,747,257  5/1998  Jensen .......................................... 435/6

OTHER PUBLICATIONS

Polley, A. et al. Identification of sex in hop (*Humulus Iupulus*) using molecular markers. Genome 40:357–361, Jun. 1997.

Sondur, S.N. et al. A genetic linkage map of papaya based on randomly amplified polymorphic DNA markers. Theor. Appl. Genet. 93:547–553, Sep. 1996.

Tibayrenc, M. et al. Genetic characterization of six parasitic protozoa: Parity between random–primer DNA typing and multilocus enzyme electrophoresis. Proc. Natl. Acad. Sci. USA 90:1335–1339, Feb. 1993.

*Primary Examiner*—Carla J. Myers
*Assistant Examiner*—Diana Johannsen
*Attorney, Agent, or Firm*—Fish & Richardson P.C.

[57] ABSTRACT

The present invention features an 831-base pair DNA fragment, and a method for the preparation of semisynthetic amplicon which is useful for determining the sex of a papaya plant.

14 Claims, No Drawings

SEQUENCE LISTING

<160> NUMBER OF SEQ ID NOS: 3

<210> SEQ ID NO 1
<211> LENGTH: 831
<212> TYPE: DNA
<213> ORGANISM: Carica papaya

<400> SEQUENCE: 1

```
gaggatccct attagtgtaa gggatgttca agaacctagc tctgatatca cctatgacat      60
ctcggtaccg aatagggcaa cggtgtctga caacataata gatatgagtg cataaaagaa     120
ctatacaaca gaagaaaagt catttcttat aaaaatttga tgtttaaata catttgagat     180
caagaacttg gtagttaaaa tatatacaag cattattata tcaacttcta tattacaaaa     240
taattgttta tcagagtaca ataattcaca tgcacttaaa ttacgctaca agttcacgaa     300
caaatccaaa caaactttaa tggtgcagtt tgagcagcag caatcttcac tttcgtatct     360
ctagggaaa tagagttggg gtgactttca taagactcag taaactctgt acggaaaata     420
gtatttaaaa tacggtaata aaggtttaaa ggttgtttat tttaaaaatg tgtcatacct     480
tttcattcaa tagagcttac cgtcagagtc cgttgcagat taaattcatt taaaatacta     540
ctaaaaagtt catacttttg gttaattgaa atacatttta aaataccaaa atttcaaaca     600
taagcagtaa aactgaatga gaaacatatt tggaaccagt ggaattatct aaacatagaa     660
agacgagaca gagtagtgag aaacatagca aactcaacat gcggtcaaaa tcatagaaat     720
aaatcaatag tcctagctag caattaaact atttggttca attacagtgt tttacagatc     780
ttcacacaaa gccattttaa cttatatcag cagagtgcaa aagggatcct c             831
```

<210> SEQ ID NO 2
<211> LENGTH: 21
<212> TYPE: DNA
<213> ORGANISM: Carica papaya

<400> SEQUENCE: 2

```
ggatccctat tagtgtaagg g                                                21
```

<210> SEQ ID NO 3
<211> LENGTH: 22
<212> TYPE: DNA
<213> ORGANISM: Carica papaya

<400> SEQUENCE: 3

```
ggatcccttt tgcactctgc tg                                               22
```

PROCESS FOR THE PREPARATION OF SEMISYNTHETIC AMPLICON USEFUL FOR SEX DETERMINATION OF THE PAPAYA PLANT

CROSS REFERENCE TO RELATED APPLICATIONS

Our copending Indian Patent Application No. 268/DEL/97 dated Mar. 31, 1997, describes a process for preparation of duplex polynucleotide useful for sex determination of papaya plant which comprises, isolating DNA from any part of a papaya plant, digesting the said DNA with known restriction enzymes at a temperature of 37±2° C., separating the fragments by electrophoresis method, hybridizing the said fragments with labeled oligonucleotide probe to get a sex specific duplex polynucleotide.

FIELD OF THE INVENTION

This invention relates to a novel DNA fragment comprising 831 bp and a process for the preparation of semisynthetic amplicon which is useful for sex determination of the papaya plant. The process also involves amplification of the target DNA in a Polymerase Chain Reaction (PCR) using synthetic oligonucleotides as primers.

BACKGROUND OF THE INVENTION

Carica papaya commonly known as papaya, is a native of tropical America. It belongs to the genus Carica, a member of family caricaceae. The plant adapts itself to diverse soil and climatic conditions, and hence is grown extensively in tropical and subtropical areas for its profitable and continuous yield of fruits. The fruits are mostly consumed ripe and are a rich source of vitamins A, B, C, and D. (Kumar et al, J. Born Natural His. Society, vol. XV no. 2, Dec 43, 252–256). A milky latex is extracted out of 25 young green fruits. This latex contains a high percentage of papain, which is one of the most valuable of plant proteolytic enzymes. Papain is of interest to many industries especially the food industry which is one of its biggest consumers. Papain is used for chillproofing beer, tenderizing meat and freeing food proteins. It is used in peptone preparation from meat and milk in bacteriological laboratories, in textile industry for degumming of silk in dairy industry for cheese preparation, in tanning industry for skin dehairing and bating of hides, in pharmaceutical industry, perfume industry and in effluent treatment. Papain is also used to produce animal feed products and recover animal wastes by digestion of proteins. (Jones et al, Process Biochemistry 9, (1976) pp. 21–22) Papaya plants are propagated through seeds. The seeds are sown in seed beds and 1–2 months old seedlings are transplanted to the field. 2–3 seedling are planted in one pit, as the sex of the seedlings is unknown. Plants attain reproductive maturity after 5–8 months. Most of the male plants are then uprooted from the field. This unnecessary cultivation and uprooting leads to wastage of time, money and labor.

The dioecious cultivars are preferred for the extraction of papain as the female yield of crude papain exceed that of hermaphrodite and also the proteolytic activity of the crude papain from female fruits is greater than hermaphrodites. (Madrigal et al., J. Sci. Food Agri 1980,31: 279–285).

Breeding programs are initiated with objectives to evolve disease resistant and true breeding papaya varieties with good quality fruits and high papain content. The dioecious nature poses problems and inconvenience to papaya breeders and growers since it takes 5–8 months to know the sex of the seedling. Unfortunately, the sex cannot be deduced from external morphology or cytology with embryonic or juvenile forms. If the sex of plants is known at the juvenile state, it would facilitate screening of the seedlings for female plants thereby saving time and economic resources and thereby helping in the breeding program.

SUMMARY OF THE INVENTION

Accordingly, the main object of the present invention is to provide a process for the preparation of a semisynthetic amplicon useful for sex determination of dioecious papaya plants.

Another objective of the present invention is to provide a process for preparation of semi-synthetic amplicon useful for sex determination of dioecious papaya plants at the juvenile stage.

Yet, another object of the invention provides a novel DNA having 831 bp nucel31 bp nucleotide sequence.

To meet the above objects, the present invention provides a novel DNA fragment comprising 831 bp and a process for the preparation of semisynthetic amplicon which is useful for sex determination of the papaya plant. The process also involves amplification of the target DNA in a Polymerase Chain Reaction (PCR) using synthetic oligonucleotides as primers.

The term "oligonucleotide" refers to a molecule comprising of two or more deoxyribonucleotides or ribonucleotides.

The term "Polymerase Chain Reaction (PCR)" is an in vitro method of nucleic acid synthesis by which a particular segment of DNA can be specifically replicated. The process of PCR involves repeated cycles of heat denaturation of the DNA, annealing of the primers to their complementary sequences and extension of the annealed primers with thermostable DNA Polymerase.

The term "primer" refers to an oligonucleotide, whether natural or synthetic, capable of acting as a point of initiation of DNA synthesis complementary to a nucleic acid strand, in the presence of four different nucleoside triphosphate and an agent for polymerization (i.e., DNA polymerase or reverse transcriptase).

The term "semisynthetic amplicon" refers to a deoxyribonucleotide polymer in double-stranded form, amplified artificially in a polymerase chain reaction. Amplifying or amplification, as used herein describes both linear and exponential increase in the number of target sequence of nucleic acid.

The term "Random Amplification of polymorphic DNA Polymerase Chain Reaction (RAPD-PCR)" as used herein described a process wherein exponential increase in the number of target sequence of nucleic acid takes place by using random decamer primers having arbitrary sequence.

The term "Sequence Tagged Site Polymerase Chain Reaction" as used herein described a process wherein exponential increase in the number of selected target sequence of nucleic acid takes place by a pair of specific primers having sequence specificity to the selected target sequence.

DETAILED DESCRIPTION OF THE INVENTION

Accordingly, the present invention provides a process for preparation semisynthetic amplicon, useful for sex determination of papaya plants, which comprises, isolating DNA from any part of a papaya plant by conventional methods, amplifying the said DNA in a conventional Random Amplification of polymorphic DNA Polymerase Chain Reaction (RAPD PCR), resolving the amplified products by conventional electrophoresis method, eluting the sex specific, double stranded and amplified product from the gel piece by known methods, cloning said product in a known vector by conventional methods, sequencing said cloned product by known methods, synthesizing the single stranded chains of synthetic oligonucleotides by known method based on the said sequence data, amplifying the said DNA in a conventional Sequence Tagged Site Polymerase Chain Reaction using a pair of single stranded chains of synthetic oligonucleotides as primers to get a sex specific semisynthetic amplicon.

In an embodiment of the present invention, the polymerase chain reaction is carried out by using a thermostable DNA polymerase enzyme.

In another embodiment of the present invention, the Random Amplification of polymorphic DNA Polymerase Chain Reaction (RAPD PCR) may be effected by using one or more single stranded oligonucleotide primers, such as known decamers.

In another embodiment of the present invention, separation of the products of Polymerase Chain Reaction may be effected by conventional electrophoresis method using agarose gel, polyacrylamide gel and mixtures thereof.

Yet another embodiment provides an isolated DNA fragment of 831 bp, described above or a complementary strand thereof, where, the said isolated DNA fragment is used for sex determination of a papaya plant. The said isolated DNA fragment may be conventionally labeled for determination of sex of papaya plants.

One more embodiment of the invention, detection of amplified resolved products is effected by known methods such as ethidium bromide staining, autoradiography, an identification of sex specific double stranded product may be effected by comparing the amplification products of RAPD-PCR of different sex forms of papaya.

In the present process, elution of the sex specific product from the gel piece may be effected by conventional elution methods, such as electroelution, freeze-thaw method, and cloning of the sex specific amplified, eluted product may be effected by using a plasmid vector 1 such as PCR product cloning vector. In addition, sequencing of the sex specific cloned product may be effected by known methods, such as, Sanger's dideoxy method.

Further, the present invention provides a process for preparing of semisynthetic amplicon, useful for sex determination of papaya plants, which comprises, synthesizing the single stranded chains of synthetic oligonucleotides by known method based on the said sequence data, amplifying the said genomic DNA of papaya plant in a conventional Sequence Tagged Site Polymerase Chain Reaction using a pair of single stranded chains of synthetic oligonucleotides as primers to get a sex specific semisynthetic amplicon. The Sequence Tagged Site Polymerase Chain Reaction is effected may be effected by using synthetic oligonucleotide primers, such as primers flanking the sequence of the said DNA fragment.

In a process of the present invention, oligonucleotide primers and nucleotides used in the polymerase chain reaction may be detectably labeled, using any reporter element that is capable of generating of detectable signal. Such detectable labels include radioactive markers such as $^{32}P$, $^{3}H$, $^{14}C$ or $^{125}I$, and non-radioactive markers, such as alkaline phosphate, biotin bromodeoxyuridine, fluorescent or chromogenic molecules etc.

In an embodiment of the present invention, elution of the sex specific amplification product from the gel piece may be effected by conventional elution methods, such as electroelution, freeze-thaw method.

In an embodiment of the present invention, cloning of the sex specific amplified, eluted product may be effected by using a plasmid vector, such as PCR product cloning vector.

In an another embodiment of the present invention, Sequence Tagged Site Polymerase Chain Reaction is effected by using synthetic oligonucleotide primers spanning the sequence of the said sex specific amplicon.

In an another embodiment of the present invention, the cloned amplicon has the following sequence.

| | | | | | |
|---|---|---|---|---|---|
| GAGGATCCCT | ATTAGTGTAA | GGGATGTTCA | AGAACCTAGC | TCTGATATCA | 50 |
| CCTATGACAT | CTCGGTACCG | AATAGGGCAA | CGGTGTCTGA | CAACATAATA | 100 |
| GATATGAGTG | CATAAAAGAA | CTATACAACA | GAAGAAAAGT | CATTTCTTAT | 150 |
| AAAAATTTGA | TGTTTAAATA | CATTTGAGAT | CAAGAACTTG | GTAGTTAAAA | 200 |
| TATATACAAG | CATTATTATA | TCAACTTCTA | TATTACAAAA | TAATTGTTTA | 250 |
| TCAGAGTACA | ATAATTCACA | TGCACTTAAA | TTACGCTACA | AGTTCACGAA | 300 |
| CAAATCCAAA | CAAACTTTAA | TGGTGCAGTT | TGAGCAGCAG | CAATCTTCAC | 350 |
| TTTCGTATCT | CTAGGGGAAA | TAGAGTTGGG | GTGACTTTCA | TAAGACTCAG | 400 |
| TAAACTCTGT | ACGGAAAATA | GTATTTAAAA | TACGGTAATA | AAGGTTTAAA | 450 |
| GGTTGTTTAT | TTTAAAAATG | TGTCATACCT | TTTCATTCAA | TAGAGCTTAC | 500 |
| CGTCAGAGTC | CGTTGCAGAT | TAAATTCATT | TAAAATACTA | CTAAAAAGTT | 550 |
| CATACTTTTG | GTTAATTGAA | ATACATTTTA | AAATACCAAA | ATTTCAAACA | 600 |
| TAAGCAGTAA | AACTGAATGA | GAAACATATF | TGGAACCAGT | GGAATTATCT | 650 |
| AAACATAGAA | AGACGAGACA | GAGTAGTGAG | AAACATAGCA | AACTCAACAT | 700 |

```
                                 -continued
GCGGTCAAAA   TCATAGAAAT   AAATCAATAG   TCCTAGCTAG   CAATTAAACT   750

ATTTGGTTCA   ATTACAGTGT   TTTACAGATC   TTCACACAAA   GCCATTTTAA   800

CTTATATCAG   CAGAGTGCAA   AAGGGATCCT   C SEQ. ID                 831
                                         NO:1
```

In a feature of the present invention, sequencing of the cloned product is effected by known method, such as Sager's chain termination method.

In a feature of the present invention synthesis synthetic oligonucleotide chains is effected by using known methods, such as phosphoramidite chemistry.

In a process of the present invention, isolation of DNA from a variety of tissues including leaf, anther, ovary, stem and root. The choice of tissue depends on many factors, including the quality of starting material required and the difficulty of isolating DNA from a particular tissue. A variety of techniques for extracting nucleic acids from biological samples are known, for example those described by Sambrook et al, Molecular Cloning-A laboratory manual, Cold Spring Harbor Laboratory, NY (1985) and by Roger & Bendich (Roger et al., 1988, PMB manual A6 1Ed) In a process of this invention oligonucleotides can be prepared by any suitable method for example, direct chemical synthesis by using phosphoramidite chemistry (Gait M. J., Oligonucleotide synthesis a practical approach, IRL press Ltd)

In a process of this invention, the amplified products of a polymerase chain reaction may be resolved by known methods for example, on agarose gel, on polyacrylamide gel, on a mixture of polyacrylamide and agarose, as described in Maniatis et al., Molecular Cloning-A Laboratory Manual, Cold Spring Harbor, N.Y., Cold Spring Harbor Laboratory, 1982.

In the process of this invention detection of the resolved amplified products on the gel can be carried out by various conventional methods for example autoradiography of the gel, staining of the gel by known methods, such as, ethidium bromide staining, silver staining as mentioned in Maniatis et al., Molecular Cloning: A Laboratory Manual, Cold Spring Harbor, N.Y., Cold Spring Harbor Laboratory, 1982.

The method of the present invention is described herein below with reference to examples which are illustrative only and should not be construed to limit the scope of the present invention in any manner.

The following example relates to the preparation of a semisynthetic amplicon useful for determination of sex in dioecious papaya plants.

EXAMPLE NO. 1

Matured male and female plants of dioecious papaya cultivar PUSA-GIANT were identified in the field. Young leaf tissue from bath male and female individuals of this cultivar were harvested and frozen in liquid nitrogen. Ten grams of the frozen 10 tissue of each sample were mechanically ground to a fine powder using pestle and mortar in liquid nitrogen.

The DNA isolations were carried out by Roger and Bendich method (Roger, 1988, PMB manual, A6:1Ed), where 15 ml of extraction buffer containing 2% CTAB (Cetyltriethyl ammonium bromide), 100 mM Tri-HCI (pH 8.0), 20 mM EDTA (pH 8.0), 1.4 M NaCl, and 1% polyvinyl pyrrolidone was added per 10 gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1 M NaCl, 10 mM Tris-HCI (pH 8.0), 1 mM EDTA pH 8.0 and was precipitated with twice the volume of absolute ethanol. The DNA precipitate was washed with 70% ethanol, centrifuged and the pellet was redisolved in TE buffer [10 mM Tris-HCI (pH 8.0), 1 mM EDTA (pH 8.0)]. For removal of RNA, the DNA was incubated at 37° C. for 1 hour with the enzyme RNaseA.

The isolated DNA was quantified spectrometrically and subjected to Random Amplification of polymorphic DNA Polymerase Chain Reaction (RAPD-PCR) with a synthetic, arbitrary, 10 bp primer (nucleotides 1–10 of SEQ ID NO: 1). The final volume of the reaction mixture was 25 μl, which contained 20ng of template DNA, 1.5 mM $MgCl_2$, 50 mM KCI, 10 mM TAPS [3-tri (hydroxymethyl) methyl amino propane sulphonic acid], 0.01% gelatin, 100 μM of each dATP, dCTP, dGTP and dTTP, 25 μM spermidine, 0.6 units of thermostable DNA polymerase and 15 pmoles of decamer primer having the sequence 5' GAGGATCCCT 3' (nucleotides 1–10 of SEQ ID NO: 1). The reaction mixture was overlaid with 30 μl of mineral oil and spun for 30 sec. at 1000 rpm.

Amplification reaction was performed in a thermocycler, where the reaction mixture was incubated at 94° C. for 5 minutes, followed by 45 cycles of 94° C. for 1 minute, 36° C. for 1 minute and 72° C. for 2 minutes each. The amplification reaction was concluded by a final extension of 72° C. for 5 minutes. The amplification products were analyzed on 1.8% neutral agarose horizontal slab gel in TAE buffer (40.0 mM Tris-acetate and 2 mM EDTA) at a constant current. After electrophoresis, gel was stained with ethidium bromide (1 μg/ml) and was visualized on a long wavelength (302 nm) WV transilluminator.

A sex specific amplicon having molecular weight of 0.8 Kb was identified in the male individual. A gel slice containing DNA of the sex specific amplicon was cut out from the gel using a sharp blade and the DNA was eluted from the gel piece as described in Maniatis et al., Molecular Cloning: A Laboratory Manual, Cold Spring Harbor, N.Y.: Cold Spring Harbor Laboratory, 1982.

100 ng of the eluted DNA was ligated to 100 ng of a PCR product cloning vector in a reaction containing, 1 μl 10× DNA ligase buffer [500 mM Tris-HCI (pH 7.4), 100 mM spermidine, 1 mg/ml BSA (Bovine Serum Albumin)], 1 μl of 1 M ATP, 1 μl of 0.1M MgCl2 and 2.0 U of the enzyme DNA ligase. Final volume of the reaction was adjusted to 10 μl by adding sterile water. The ligation reaction was carried out 16 C for 16 hours and the ligated products were directly transformed into the competent cells of E.coli. The transformed E.coli cells were plated on LB (Luria-Bertani) medium [Bacto typtone 10 gm/lit, Bacto yeast extract 5 gm/lit, Sodium chloride 10 gm/lit] containing the antibiotic ampicillin (100 μg/ml). Resulting colonies were screened for the presence of the recombinants as described in Maniatis et al., Molecular Cloning: A Laboratory Manual, Cold Spring Harbor, N.Y.: Cold Spring Harbor laboratory, 1982. The plasmid DNA was isolated by inoculating a colony positive for the insert in 1 m LB medium containing the antibiotic ampicillin (100 μg/ml). The culture was grown at 37° C. for 16 hrs with constant shaking at 175rpm. The culture was spun in 1.5ml plastic tube for 10 minutes to pellet the cells and the supernatant was discarded. The cell pellet was suspended in a 10 μl solution of GTE buffer (50 mM Glucose, 25 mM Tris-HCl (pH 8.0), and 10 mM EDTA (pH 8.0)], vortexed and incubated at room temperature for ten minutes. 200 μl of freshly prepared solution containing 1% SDS and 0.2N NaOH was added to the cell suspension, mixed well by tapping the tube and incubated on ice for ten minutes and further purified as described by Maniatis et al. [Molecular Cloning: A Laboratory Manual, Cold Spring Harbor, N.Y.: Cold Spring Harbor Laboratory, 1982]

The cloned PCR fragment was sequenced by Sager's dideoxy chain termination method, as described by Sager et al., PNAS 74, 1977: 54–83.

To denature the template DNA, 2 μg of plasmid DNA was dried in an eppendorf tube and dissolved in 40 μl denaturation buffer (0.2M NaOH, 0.2 mM EDTA (pH 8.0) and kept at 37° C. for 30 minutes. 40 μl of 3M Sodium acetate, pH 5.2 was added, followed by 100 μg of chilled ethanol and precipitated for 30 minutes at 70° C. The sample was spun at 10,000 rpm for 10 minutes at 4° C. Supernatant was discarded and pellet was washed with 70% ethanol, dried and dissolved in 7 μl of sterile water.

To anneal the sequencing primer to the template DNA, 1 μl of sequencing primer and 2 μl of 5× reaction buffer were added to the template DNA and incubated at 65° C. for 2 minutes.

The labeling reaction was carried out by adding 1 μl DTT(0.1M), 2 μl labeling nucleotide mix (7.5 μm dGTP, 7.5 μm dTTP, 7.5 μl dCTP), 5 μCi of a-$^{32}$P dATP and 0.6 units of enzyme to the annealed template primer. The sample was incubated for 5 minutes at room temperature.

2 μl of dideoxynucleotide mixture (ddGTP, ddCTP, ddATP and ddTTP) was taken in four labeled tubes and warmed to 37° C. for 2 minutes. 3.5 μl of the template primer mixture was added to each of the labeled tubes, mixed and incubated at 37° C. for 5 minutes. After the incubation, 4 μl of formamide buffer (75% Formamide, 20 mM EDTA, 0.05% Bromophenol Blue, 0.05% Xylene Cyanol FF) was added to stop the reaction.

The sequencing reaction was then resolved on a 6%, 0.4 mm thick, denaturing polyacrylamide gel. Electrophoresis was carried out at a constant voltage (2000V) in 1×TBE buffer (89 mM Tris-borate and 2 mM EDTA). After the electrophoresis, the gel was covered in thin plastic sheet and exposed to an X-ray film at 70° C. for 16 hours.

Sequencing of the cloned amplicon revealed a sequence as shown in the SEQ ID NO: 1.

SEQ ID NO: 1

| | | | | | |
|---|---|---|---|---|---|
| GAGGATCCCT | ATTAGTGTAA | GGGATGTTCA | AGAACCTAGC | TCTGATATCA | 50 |
| CCTATGACAT | CTCGGTACCG | AATAGGGCAA | CGGTGTCTGA | CAACATAATA | 100 |
| GATATGAGTG | CATAAAAGAA | CTATACAACA | GAAGAAAAGT | CATTTCTTAT | 150 |
| AAAAATTTGA | TGTTTAAATA | CATTTGAGAT | CAAGAACTTG | GTAGTTAAAA | 200 |
| TATATACAAG | CATTATTATA | TCAACTTCTA | TATTACAAAA | TAATTGTTTA | 250 |
| TCAGAGTACA | ATAATTCACA | TGCACTTAAA | TTACGCTACA | AGTTCACGAA | 300 |
| CAAATCCAAA | CAAACTTTAA | TGGTGCAGTT | TGAGCAGCAG | CAATCTTCAC | 350 |
| TTTCGTATCT | CTAGGGGAAA | TAGAGTTGGG | GTGACTTTCA | TAAGACTCAG | 400 |
| TAAACTCTGT | ACGGAAAATA | GTATTTAAAA | TACGGTAATA | AAGGTTTAAA | 450 |
| GGTTGTTTAT | TTTAAAAATG | TGTCATACCT | TTTCATTCAA | TAGAGCTTAC | 500 |
| CGTCAGAGTC | CGTTGCAGAT | TAAATTCATT | TAAAATACTA | CTAAAAAGTT | 550 |
| CATACTTTTG | GTTAATTGAA | ATACATTTTA | AAATACCAAA | ATTTCAAACA | 600 |
| TAAGCAGTAA | AACTGAATGA | GAAACATATT | TGGAACCAGT | GGAATTATCT | 650 |
| AAACATAGAA | AGACGAGACA | GAGTAGTGAG | AAACATAGCA | AACTCAACAT | 700 |
| GCGGTCAAAA | TCATAGAAAT | AAATCAATAG | TCCTAGCTAG | CAATTAAACT | 750 |
| ATTTGGTTCA | ATTACAGTGT | TTTACAGATC | TTCACACAAA | GCCATTTTAA | 100 |
| CTTATATCAG | CAGAGTGCAA | AAGGGATCCT | C SEQ ID NO: 1 | | 831 |

From the sequence data, the primers were designed to amplify the entire sequence of the amplicon. The sequence of the synthetic oligonucleotide primers is as given in sequence identity no. 2 and sequence identity no. 3.

SEQ ID NO: 2
5'GGATCCCTASTAGTGTIUGGG 3'
SEQ ID NO: 3
5'GGATCCCTTTTGCACTCTGCTG3'

The isolated DNA of the cultivar PUSA-GIANT was subjected to sequence tagged polymerase chain reaction using the pair of synthetic oligonucleotide primers as mentioned in sequence identity no. 2 and sequence identity no. 3. The reaction mixture contained, 50 ng of template DNA, 1.5 mM MgCl2, 50 mM KCl, 10 mM TAPS [3-tri (hydroxymethyl) methyl amino propane sulphonic acid], 0.01% gelatin, 100 μM of each dATP, dCTP, dGTP and dTTP, 25 μlM spermidine, 0.6 units of thermostable DNA polymerase, 5.6% Formamide. 15 pmoles of each of synthetic oligonucleotide primers and the final volume was made up to 25 μl by adding sterile water. The reaction mixture was then overlaid with 30 μl of mineral oil and spun for 30 sec. at 1000 rpm.

Amplification reaction was performed in a thermocycler, where the reaction mixture was incubated at 94° C. for 5 minutes, followed by 30 cycles of 94° C. for 1 minute, 60° C. for 1 minute and 72° C. for 2 minutes each. The amplification reaction was concluded by a final extension of 72 C for 5 minutes. The amplification product was analyzed on a 1.5% neutral agarose horizontal slab gel in TAE buffer, (0.09M Tris-acetate and 2 mM EDTA) at a constant current. After electrophoresis, gel was stained with ethidlum bromide (1 μ/ml) and was visualized on a long wavelength (302 nm) UV transilluminator.

It was observed, that on using the said pair of synthetic oligonucleotides in a sequence tagged polymerase chain reaction, only a single amplicon of 831 bp in size was amplified sex specifically and hence could accurately identify male papaya plants.

The following examples 2 and 3 relate to the determination of sex in dioecious cultivars of papaya using semisynthetic amplicon.

EXAMPLE NO. 2

Matured male and female plants of dioecious papaya cultivars namely, CO-2, CO-4, CO-5, CO-6 MF-1, PANT-1, WASHINGTON, PUSA-GIANT, and PUSA-DWARF were identified in the field. Young leaf tissue from both male and female individuals of these cultivars was harvested frozen in liquid nitrogen. Ten grams of this frozen tissue of each sample was mechanically ground to a fine powder using a pestle and mortar in liquid nitrogen.

The DNA isolations were carried out by Roger and Bendich method (Roger, 1988, PMB manual, A6:1Ed), where 15 ml of extraction buffer containing 2% CTAB (Cetyltriethyl ammonium bromide), 100 mM Tris-HCI (pH 8.0), 20 mM EDTA (pH 8.0), 1.4 M NaCl, and 1% polyvinyl pyrrolidone was added per 10 gm of frozen tissue. Equal volume of chloroform:Isoamyl alcohol (24:1) mixture, was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1M NaCl, 10 mM Tris-HCI (pH 8.0), 1 mM EDTA (pH 8.0) and was precipitated with twice the volume of absolute ethanol. The DNA precipitate was washed with 70% ethanol, centrifuged and the pellet was redissolved in TE buffer [10 mM Tris-HCI (pH 8.0), 1 mM EDTA (PH 8.0)]. For removal of RNA, the DNA was incubated at 37 C for 1 hour with the enzyme RNaseA.

The isolated DNA was quantified spectrophotometrically and subjected to polymerase chain reaction with a pair of synthetic oligonucleotide primers having the sequence 5'GGATCCCTATTAGTGTAAGGG3' (SEQ ID NO: 2)
and 5'GGATCCCTTTTGCACTCTGCTG3' (SEQ ID NO: 3)

The reaction mixture contained, 50 ng of template DNA, 1.5 mM MgCl2, 50 mM KCl, 10 mM TAPS [3-tri ((hydroxymethyl) methyl amino propane sulphotiic acid], (0.01% gelatin, 100 ml of each dATP, dCTP, dGTP and dTTP, 25 mM spermicline, 0.6 units of thermostable DNA polymerase, 5.6% Formamide, 15 pmoles of each of synthetic oligonucleotide primers and the final volume was made up to 25ml by adding sterile water. The reaction mixture was then overlaid with 30 μl. of mineral oil and spun for 30 sec. at 1000 rpm.

Amplification reaction was performed in a thermocycler, where the reaction mixture was incubated at 94° C. for 5 minutes, followed by 30 cycles of 94° C. for 1 minute, 60° C. for 1 minute and 72° C. for 2 minutes each. The amplification reaction was concluded by a final extension of 72° C. for 5 minutes. The amplification product was analyzed on 1.5% neutral agarose horizontal slab gels in TAE buffer, (0.09M Tris-acetate and 2 mM EDTA) at a constant current. After electrophoresis, gels were stained in dark with ethidium bromide (1 ug/ml) and were visualized on a long wavelength (302 nm) UV transilluminator.

It was observed that on using the said pair of synthetic oligonucleotides in a polymerase chain reaction, only a single amplicon of 831 bp in size was amplified sex specially and hence could accurately identify male papaya .a plants in all the dioecious cultivars tested.

EXAMPLE NO. 3

Male and female plants of dioecious papaya cultivars namely, CO-2, CO-4, CO-5, CO-6, MF-1, PANT-1, WASHINGTON, PUSA-GIANT and PUSA-DWARF were identified in the field. Leaf tissue from male and female individuals of these cultivars was harvested in the form of leaf discs and then frozen in liquid nitrogen, in sterile, 1.5 ml microcentrifuge tubes.

The leaf discs, weighing 10 mg were used for DNA isolation, which was carried out by modifying the method described by Thompson et al. Blotechniques, Vol. 19, No. 3, 1995, 394–400. 20 μl of extraction buffer consisting of 100 mM TrisHCl (pH 9.5), IM KCl and 10 Mm EDTA was added per 10 mg of frozen tissue and vortexed briefly. The tubes were further incubated at 95° C. for 10 min in a dry bath. The contents were mixed intermittently by inverting and tapping the tubes. After incubation, the tubes were placed on ice for 5 min and then centrifuged at 10,000 rpm for 10 min in a microfuge. From each sample tube, 4 μl of the supernatant was transferred to a fresh tube and diluted 50 fold by adding 196 μl of sterile water.

The diluted supernatant was directly used in the polymerase chain reaction. The final volume of reaction mixture was 25 μl, which contained 20 ng of template DNA, 1.5 Mm MgCl2, 50 Mm KCl, 10 Mm TAPS [3-tri (hydroxymethyl) methyl amino propane sulphonic acid], 0.01% gelatin, 100 μM of each dNTP, 25 μM spermidine, 0.6 Units of thermostable DNA polymerase, 4.0% Formamide and 15 pmoles of each cf synthetic oligonucleotide primers. The final volume of reaction mixture was made up of 25 μl by adding sterile water, overlaid with 50 μl of mineral oil and spun for 30 sec. at 1000 rpm.

Amplification reaction was performed in a thermocycler. The reaction mixture was initially incubated at 94° C. for 5 minutes, followed by 30 cycles of 94° C. for 1 minute, 55° C. for 1 minute and 72° C. for 2 minutes each. The amplification reaction was concluded by a final extension of 72° C. for 5 minutes. the amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide 1 ug/ml and was visualized on a long wavelength (302 nm) UV transilluminator.

It was observed, that on using the said pair of synthetic oligonucleotides in a polymerase chain reaction, only a single amplicon of 831 bp in size was amplified sex specifically and hence could accurately identify male papaya plants in all the dioecious cultivars tested.

The examples 4 and 5 relate to the usage of semisynthetic amplicon in sex determination of papaya plant using various tissues of papaya plant.

EXAMPLE NO. 4

Matured male and female plants of variety CO-2 were identified in the field. Tissue of leaf, anther and ovary were harvested from male and female plants respectively and frozen in liquid nitrogen. On gram of frozen tissue of each sample was mechanically ground to a fine powder using a pestle and mortar in liquid nitrogen.

The DNA isolations were carried out by Roger and Bendich method (Roger, 1988, PMB manual, A6:1Ed), where 15 ml of extraction buffer containing 2% CTAB (Cetyltriethyl ammonium bromide), 100 mM Tris-HCI (pH 8.0), 20 mM EDTA (pH 8.0), 1.4 M Naci, and 1% polyvinyl pyrrolidone was added per 10 gm of frozen tissue. Equal volume of chloroform isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing, 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1M NaCl, 10 mM Tris-HCI (pH 8.0) 1 mM EDTA (pH 8.0) ] and was precipitated with twice the volume of absolute ethanol. The DNA precipitate was washed with 70% ethanol, centrifuged and the pellet was redisolved in TE buffer [10 mM Tris-HCI (pH 8.0), 1 mM EDTA (pH 8.0)]. For removal of RNA, the DNA was incubated at 37° C. for 1 hour with the enzyme RNaseA.

The reaction mixture contained, 50 ng of template DNA, 1.5 mM MgCl2, 50 mM KCI, 10 mM TAPS [3-tri (hydroxmethyl) methyl amino propane sulphonic acid], 0.01% gelatin, 100 µM of each dATP, dCTP, dGTP and dTTP, 25 µM spermidine, 0.6 units of thermostable DNA polymerase, 5.6% Formamide, 15 pmoles of each of synthetic oligonucleotide primers and the final volume was made up to 25 µl by adding sterile water. The reaction mixture was then overlaid with 30 µl of mineral oil and spun for 30 sec. at 1000 rpm.

Amplification reaction was performed in a thermocycler, where the reaction mixture was incubated at 94° C. for 5 minutes, followed by 30 cycles of 94° C. for 1 minute, 60° C. for 1 minute and 720 for 2 minutes each. The amplification reaction was concluded by a final extension of 72° for 5 minutes. The amplification product was analyzed on 1.5% neutral agarose horizontal slab gels in TAE buffer, (0.09 Tris-acetate and 2 mM EDTA) at a constant current. After electrophoresis, gels were stained in dark with ethidium bromide (1 µg/ml) and were visualized on a long wavelength (302 nm) UV transilluminator.

It was observed that, on using the said pair of synthetic oligonucleotides in a polymerase chain reaction, only a single amplicon of 831 bp in size was amplified sex specifically in the tissue of anther of a male plant.

EXAMPLE NO. 5

Matured male and female plants of variety CO-2 were identified in the field. Tissue of anther and ovary was harvested from male and female plants respectively and frozen in liquid nitrogen. Leaf tissue from male and female individuals of these cultivars was harvested in the form of leaf discs and then frozen in liquid nitrogen, in sterile, 1.5 ml microcentrifuge tube.

The leaf discs, weighing 10 mg were used for DNA isolation, which was carried out by modifying the method described Thompson et al (Biotechniques, Vol. 19, No. 3, 1995, 394–400). 20 µl of extraction buffer consisting of 100 mM Tris-HCI (pH 9.5), 1M KCL and 10 mM EDTA was added per 10 mg of frozen tissue and vortexed briefly. The tubes were further incubated at 95° C. for 10 min. in a dry bath. The contents were mixed intermittently by inverting and tapping the tubes. After incubation, the tubes were placed on ice for 5 min. and then centrifuged at 10,000 rpm for 10 min. in a microfuge. From each sample tube, 4 µl of the supernatant was transferred to a fresh tube and diluted 50 fold by adding 198 µul of sterile water.

The diluted supernatant was directly used in the polymerase chain reaction. The final volume of the reaction mixture was 25 µl, which contained 5 µl of the diluted supernatant, 1.5 mM MgCl2, 50 mM KCI, 10 mM TAPS [3-tri (hydroxymethyl) methyl amino propane sulphonic acid], 0.01% gelatin, 100 µM of each dNTP, 25 µM spermidine, 0.6 Unites of thermostable DNA polymerase, 4.0% Formamide and 15 pmoles of each of synthetic oligonucleotide primers. The final volume of the reaction mixture was made up to 25 µl by adding sterile water, overlaid with 25 µl of mineral oil and spun for 30 sec. at 1000 rpm.

Amplification reaction was performed in a thermocycler. The reaction mixture was initially incubated at 94° C. for 5 minutes, followed by 30 cycles of 94° C. for 1 minute, 55° C. for 1 minute and 72° C. for 2 minutes each. The amplification reaction was concluded by a final extension of 720 for 5 minutes. The amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide (1 µg/ml) and was visualized on a long wavelength (302 nm) UV transilluminator.

It was observed that, on using the said pair of synthetic oligonucleotides in a polymerase chain reaction, only a single amplicon of 831 bp in size was amplified sex specifically in the tissue of anther of a male plant. Following examples 6 and 7 relate to the sex determination in wild species of the genus Carica, using a semisynthetic amplicon.

EXAMPLE NO. 6

Male and female plants of wild species, *Carica cauliflora* were identified in the field. Young leaf tissue from both male and female individuals was harvested and frozen in liquid nitrogen. Ten grams of this frozen tissue of each sample was mechanically ground to a fine powder using a pestle and mortar in liquid nitrogen.

The DNA isolations were carried out by Roger and Bendich method (Roger, 1988, PMB manual, A6:1Ed), where 15 ml of extraction buffer containing 2% CTAB (Cetyltriethyl ammonium bromide), 100 mM Tri-HCI (pH 8.0), 20 mM EDTA (pH 8.0), 1.4 M Nacl, and 1% polyvinyl pyrrolidone was added per 10 gm of frozen tissue. Equal volume of chloroform isoarryl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1M NaCl, 10 mM Tris-HCl (pH 8.0) 1 mM EDTA (pH 8.0)] and was precipitated with twice the volume of absolute ethanol. The DNA precipitate was washed with 70% ethanol, centrifuted and the pellet was redisolved in TE buffer [10 mM Tris-HCI (pH 8.0), 1 mM EDTA (pH 8.0)]. For removal of RNA, the DNA was incubated at 37° C. for 1 hour with the enzyme RNaseA.

The reaction mixture contained, 50 ng of template DNA, 1.5 mM MgCl2, 50 mM KCI, 10 mM TAPS [3-tri (hydroxmethyl) methyl amino propane sulphonic acid], 0.01% gelatin, 100 µM of each dATP, dCTP, dGTP and dTTP, 25 µM spermidine, 0.6 units of thermostable DNA polymerase, 5.6% Formamide, 15 pmoles of each of synthetic oligonucleotide primers and the final volume was made up to 25 µl by adding sterile water. The reaction mixture was then overlaid with 30 µl of mineral oil and spun for 30 sec. at 1000 rpm.

Amplification reaction was performed in a thermocycler, where the reaction mixture was incubated at 94° C. for 5 minutes, followed by 30 cycles of 94° C. for 1 minute, 60° C. for 1 minute and 72° C. for 2 minutes each. The amplification reaction was concluded by a final extension of 72° for 5 minutes. The amplification products were then analyzed on 1.5% neutral agarose horizontal slab gels in TAE buffer, (0.09M Tris-acetate and 2 mM EDTA) at a constant current. After electrophoresis, the gel was stained in dark with ethidium bromide (1 g/ml) and were visualized on a long wavelength (302 nm) UV transilluminator It was observed that, on using the said pair of synthetic oligonucleotides in a polymerase chain reaction, only a singe amplicon of 831 bp in size was amplified sex specifically and hence could accurately identify male papaya plants of the dioecious wild species tested.

EXAMPLE NO. 7

Male and female plants of wild species, *Carica cauliflora* were identified in the field. Leaf tissue from male and female individuals was harvested in the form of leaf discs and then frozen in liquid nitrogen, in sterile, 1.5 ml microcentrifuge tubes.

The leaf discs, weighing 10 mg were used for DNA isolation, which was carried out by modifying the method described by Thompson et al (Biotechniques, Vol.19, No. 3, 1995, 394–400). 20 µl of extraction buffer consisting of 100 mM Tris-HCI (pH 9.5), 1M KCI and 10 mM EDTA was added per 10 mg of frozen tissue and vortexed briefly. The tubes were further incubated at 95° C. for 10 min. in a dry bath. The contents were mixed intermittently by inverting and tapping the tubes. After incubation, the tubes were placed on ice for 5 min. and then centrifuged at 10,000 rpm for 10 min. in a microfuge. From each sample tube, 4 µl of the supernatant was transferred to a fresh tube and diluted 50 fold by adding 196 µl of sterile water.

The diluted supernatant was directly used in the polymerase chain reaction. The final volume of the reaction mixture was 25 µl, which contained 5 µl of the diluted supernatant, 1.5 mM MgCl2, 50 mM KCL, 10 mM TAPS [3 tri (hydroxymethyl) methyl arnino propane sulphonic acid], 0.01% gelatin, 100 µM of each dNTP, 25 µM spermidine, 0.6 Units of thermostable DNA polymerase, 4.0% Formamide and 15 pmoles of each synthetic oligonucleotide primers. The final volume of the reaction mixture was made up to 25 µl by adding sterile water, overlaid with 25 µl of mineral oil and spun for 30 sec. at 1000 rpm.

Amplification reaction was performed in a thermocycler. The reaction mixture was initially incubated at 94° C. for 5 minutes, followed by 30 cycles of 94° C. for 1 minute, 55° C. for 1 minute and 72° C. for 2 minutes each. The amplification reaction was concluded by a final extension of 72° for 5 minutes. The amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide (1 µg/ml) and were visualized on a long wavelength (302 nm) UV transilluminator.

It was observed that, on using the said pair of synthetic oligonucleotides in a polymerase chain reaction, only a single amplicon of 831 bp in size was amplified sex specifically and hence could accurately identify male papaya plants of the dioecious wild species tested.

The following examples 8 and 9 relate to the sex determination of unknown papaya plants at the seedling stage, using a semisynthetic amplicon.

EXAMPLE NO. 8

Fifty seedling plants were serially numbered 1–50 in the field. Young leaf tissue of 24 randomly selected individuals was harvested frozen in liquid nitrogen. One gram of this frozen tissue of each sample was mechanically ground to a fine powder using a pestle and mortar in liquid nitrogen.

The DNA isolations were carried out by Roger and Bendich method (Roger, 1988, PMB manual, A6:1Ed), where 15 ml of extraction buffer containing 2% CTAB (cetyltriethyl ammonium bromide), 100 mM Tri-HCI (pH 8.), 20 mM EDTA (pH 8.0), 1.4 M Naci, and 1% polyvinyl pyrrolidone was added per 10 gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing 1% CTAB, 50 mM Tris-HCI (pH 8.0) and 10 mM EDTA (pH 8.0) was added, mixed gently and centrifuged at 10,000 rpm. The DNA pellet was dissolved in high salt TE buffer [1M NaCl, 10 mM Tris-HCI (pH 8.0) 1 mM EDTA (pH 8.0)] and was precipitated with twice the volume of absolute ethanol. The DNA precipitate was washed with 70% ethanol, centrifuged and the pellet was redissolved in TE buffer [10 mM Tris-HCI (pH 8.0), 1 mM EDTA (pH 8.0)]. For removal of RNA, the DNA was incubated at 37° C. for 1 hour with the enzyme RNaseA.

The reaction mixture contained, 50 ng of template DNA, 1.5 mM MgCl2, 50 mM KCI, 10 mM TAPS [3-tri (hydroxymethyl) methyl amino propane sulphonic acid], 0.01% gelatin, 100 µM of each dATP, dCTP, dGTP and dTTP, 25 µM spermidine, 0.6 units of thermostable DNA polymerase, 5.6% Formamide, 15 pmoles of each of synthetic oligonucleotide primers and the final volume was made up to 25 µl by adding sterile water. The reaction mixture was then overlaid with 30 µl of mineral oil and spun for 30 sec. at 1000 rpm.

Amplification reaction was performed in a thermocycler where the reaction mixture was initially incubated at 94° C. for 5 minutes, followed by 30 cycles of 94° C. for 1 minute, 60° C. for 1 minute and 72° C. for 2 minutes each. The amplification reaction was concluded by a final extension of 72° for 5 minutes. The amplification products were then analyzed on 1.5% neutral agarose horizontal slab gels in TAE buffer, (0.09M Tris-acetate and 2 mM EDTA) at a constant current. After electrophoresis, the gel was stained in dark with ethidium bromide (1 μg/ml) and were visualized on a long wavelength (302 nm) UV transilluminator.

The results obtained were compared with the sex of the plant observed after flowering. The results are tabulated in the following table.

| Serial No. of seedling plant | Sex of the plant determined by the process | Sex of the plant observed (in the field) after flowering |
| --- | --- | --- |
| 4 | Male | Male |
| 5 | Female | Female |
| 8 | Male | Female |
| 10 | Male | Male |
| 12 | Female | Female |
| 13 | Female | Female |
| 16 | Female | Female |
| 18 | Male | Male |
| 22 | Male | Male |
| 26 | Male | Male |
| 27 | Male | Male |
| 29 | Female | Female |
| 30 | Male | Male |
| 32 | Female | Female |
| 33 | Female | Female |
| 34 | Male | Male |
| 36 | Female | Female |
| 37 | Male | Male |
| 38 | Male | Male |
| 41 | Female | Female |
| 43 | Male | Male |
| 47 | Female | Female |
| 49 | Female | Female |
| 50 | Female | Female |

EXAMPLE NO. 9

Fifty seedling plants were serially numbered 1–50 in the field. Young leaf tissue of 22 randomly selected individuals was harvested frozen in liquid nitrogen. Leaf tissue from these individuals was harvested in the form of leaf discs and then frozen in liquid nitrogen in sterile, 1.5 ml microcentrifuge tubes.

The leaf discs, weighing 10 mg were used for DNA isolation, which as carried out by modifying the method described by Thompson et al (Biotechniques, Vol. 19, No. 3, 1995, 349–400). 20 μl of extraction buffer consisting of 100 mM Tris-HCl (pH 9.5) 1 M KCL and 10 mM EDTA was added per 10 mg of frozen tissue and vortexed briefly. The tubes were further incubated at 95° C. for 10 min. in a dry bath. The contents were mixed intermittently by inverting and tapping the tubes. After incubation, the tubes were placed on ice for 5 min and then centrifuged at 10,000 rpm for 10 min in a microfuge. From each sample tube, 4 μl of the supernatant was transferred to a fresh tube and diluted 50 fold by adding 196 μl of sterile water.

The diluted supernatant was directly used in the polymerase chain reaction. The final volume of the reaction mixture was 25 μl, which contained 5 μl of the diluted supernatant, 1.5 mM MgCl2, 50 mM KCl, 10 mM TAPS [3-tri (hydroxmethyl) methyl, amino propane sulponic acid], 0.01% gelatin, 100 μM of each dNTP, 25 μM spermidine, 0.6 Units of thermostable DNA polymerase, 4.0% Formamide and 15 pmoles of each of synthetic oligonucleotide primers. The final volume of the reaction mixture was made up to 25 μl by adding sterile water overlaid with 25 μl of mineral oil and spun for 30 sec. at 1000 rpm.

Amplification reaction was performed in a thermocycler. The reaction mixture was initially incubated at 94° C. for 5 minutes, followed by 30 cycles of 94° C. for 1 minute, 55° C. for 1 minute and 72° C. for 2 minutes each. The amplification reaction was concluded by a final extension of 72° C. for 5 minutes. The amplification products were then analyzed on 1.5% neutral agarose horizontal slab gels in TAE buffer, (0.09M Tris-acetate and 2 mM EDTA) at a constant current of 40 mA. After electrophoresis, the gel was stained in dark with ethidium bromide (1 μg/ml) and were visualized on a long wavelength (302 nm) UV transilluminator.

The results obtained were compared with the sex of the plant observed after flowering. The results are tabulated in the following table.

| Serial No. of seedling plant | Sex of the plant determined by the process | Sex of the plant observed (in the field) after flowering |
| --- | --- | --- |
| 1 | Male | Male |
| 4 | Male | Male |
| 5 | Female | Female |
| 6 | Male | Male |
| 8 | Female | Female |
| 9 | Male | Male |
| 10 | Male | Male |
| 13 | Male | Female |
| 14 | Male | Male |
| 15 | Female | Female |
| 16 | Female | Female |
| 17 | Female | Female |
| 18 | Male | Male |
| 19 | Female | Female |
| 21 | Female | Female |
| 23 | Female | Female |
| 24 | Male | Male |
| 26 | Male | Male |
| 29 | Female | Female |
| 31 | Male | Male |
| 32 | Female | Female |
| 33 | Female | Female |
| 34 | Male | Male |

The following example relates to the gel blot analysis of the semisynthetic amplicon.

EXAMPLE NO. 10

Matured male and female plants of dioecious papaya cultivars namely, CO-2, WASHINGTON and PUSA-GIANT were identified in the field. Young leaf tissue from both male and female individuals of these cultivars was harvested frozen in liquid nitrogen. Ten grams of this frozen tissue of each sample was mechanically ground to a fine powder using a pestle and mortar in liquid nitrogen.

The DNA isolations were carried out by Roger and Bendich method (Roger, 1988, PMB manual, A6:1Ed), where 15 ml of extraction buffer containing 2% CTAB (Ctyltriethyl ammonium bromide), 100 mM Tri-HCl (pH 8.), 20 mM EDTA (pH 8.0), 1.4 M Naci, and 1% polyvinyl pyrrolidone was added per 10 gm of frozen tissue. Equal volume of chloroform:isoamyl alcohol (24:1) mixture was added and mixed thoroughly to form an emulsion, which was centrifuged for 10 minutes at 10,000 rpm in a SS34 rotor. To the supernatant, equal volume of CTAB precipitation buffer containing 1% CTAB, 50 mM Tris-HCl (pH 8.0) and 10 mM EDTA (pH 8.0) was added, mixed gently and centrifuged at 10,000 rpm. The DNA pellet was dissolved in high salt TE buffer [1M NaCl, 10 mM Tris-HCl (pH 8.0) 1 mM EDTA (pH 8.0)] and was precipitated with twice the volume of absolute ethanol. The DNA precipitate was washed with 70% ethanol, centrifuged and the pellet was redissolved in TE buffer [10 mM Tris-HCl (pH 8.0), 1 mM EDTA (pH 8.0)]. For removal of RNA, he DNA was incubated at 37° C. for 1 hour with the enzyme RNaseA.

The isolated DNA was quantified spectrophotometrically and subjected to digestion with restriction enzyme HaeIII. Ten micrograms of DNA was incubated with the enzyme HaeIII at 37° C. for 16 hours. The salt concentrations of buffer were 10 mM Tris.HCl (pH. 7.0), 50 mM Sodium Chloride, lOmM Magnesium Chloride and 5 mM Beta-Mercapfoethanol. The reaction was heat terminated by incubating at 95° C. for 10 minutes. The digests were analyzed on 1.2% neutral agarose horizontal slab gel in TPE, (0.09M Tris-phosphate and 2mM EDTA buffer), at a constant current of 40 mA for 16 hours. After electrophoresis, gel was stained in dark with ethidium bromide($\mu$g/ml) and was visualized on a long wavelength (302 nm) UV transilluminator.

To transfer the resolved DNA fragments onto a solid support, the gel was placed on to the vacuum blotting apparatus on top of the nylon membrane and a pressure of 55 lb was maintained in the vacuum pump. For depurination of DNA, the gel was treated with 0.25N HCl for 10 minutes and then it was denatured in a solution containing 1.5M NaCl and 0.5N NaOH for 15 minutes. Neutralization of DNA was achieved by treating the gel in a solution of 1M Tris-HCl (pH 8.0) and 1.5M NaCl for 15 minutes at room temperature. The transfer of DNA onto the membrane was carried out for one hour in 20× SSPE [3.0 M Sodium chloride (NaCl), 0.20 M Sodium dihydrogen orthophosphate (($NaH_2PO_4$) and 0.04M ethylene diamine tetra acetic acid disodium salt (EDTA)]. Membrane was then rinsed in 2× SSPE [0.3M Sodium Chloride (NaCl), 0.02M Sodium dihydrogen orthophosphate (($Na_2PO_4$) and 0.04M ethylene diamine tetra acetic acid disodium salt (EDTA)], air dried and baked for two hours at 80° C. in a vacuum oven. The DNA isolated from a male papaya plant was subjected to polymerase chain reaction with a pair of synthetic oligonucleotide primers having the sequence

5'GGATCCCTATTAGTGTAAGGG3' (SEQ ID NO: 2)

and 5'GGATCCCTTTTGCACTCTGCTG3' (SEQ ID NO: 3)

The reaction mixture contained, 50 ng of template DNA, 1.5 mM MgCl2, 50 mM KCl, 10 mM TAPS [3-tri (hydroxymethyl) methyl amino propane sulphonic acid], 0.01% gelatin, 100 $\mu$M of each dATP, dCTP, dGTP and dTTP, 25 $\mu$M spermidine, 0.6 units of thermostable DNA polymerase, 5.6% Formamide, 15 pmoles of each of synthetic oligonucleotide primers and the final volume was made up to 25 $\mu$l by adding sterile water. The reaction mixture was then overlaid with 30 $\mu$l of mineral oil and spun for 30 sec. at 1000 rmp.

Amplification reaction was performed in a thermocycler, where the reaction mixture was incubated at 94° C. for 5 minutes, followed by 30 cycles of 94° C. for 1 minute, 60° C. for 1 minute and 72° C. for 2 minutes each. The amplification reaction was concluded by a final extension of 72° C. for 5 minutes. The amplification products were then analyzed on 1.5% neutral agarose horizontal slab gels in TAE buffer, (0.09M Tris-acetate and 2 mM EDTA) at a constant current. 100 ng of the amplified DNA was radioactively labeled by multiprime labeling method as described in Maniatis et al, Molecular Cloning: A Laboratory Manual, Cold Spring Harbor, N.Y.: Cold Spring Harbor Laboratory, 1982.

100 ng of the amplified DNA was dissolved in 10 $\mu$l of TE [10 mM Tris (pH 8.0), 1 mM EDTA], denatured by boiling for 10 minutes and was immediately chilled on ice. To label the denatured DNA, 5 $\mu$l randomprimer mix, 5 $\mu$l labeling buffer, 4 $\mu$l each of dATP, dGTP and dTTP, 5 $\mu$l (50 $\mu$CI) of a-$^{32}$P-dATP (specific activity 3000 Ci/m mole) and 2$\mu$ klenow fragment (4 U) were added and the final volume was made to 50 $\mu$l with sterile water. Reaction was carried out at 37° C. for 2 hours and terminated by adding 10× stop dye (10% SDS, 125 mM EDTA, 0.25% Bromophenol blue) to a final concentration of 1×.

The labeled DNA probe was separated from unincorporated nucleotides by purification using spun column chromatography. A 1.5 ml microfuge tube was packed with gel beads by centrifugation. The entire mixture containing labeled probe and free nucleotides was loaded on this exclusion column and spun at 1000 rpm for 10 seconds. 100 $\mu$l of TE was added on top of the column and again spun at 1000 rpm for 10 seconds. The procedure was repeated thrice. The eluted probe was denatured by boiling it for 10 minutes and immediately chilling on ice. This denatured probe was further used for hybridization.

To prevent the non-specific binding of the probe onto membranes, filters were prehybridized for two hours. Prehybridization was carried out in heat sealed plastic bags containing the following mixture: 5× SSPE [0.75M Sodium chloride (NaCl). 0.05 Sodium dihydrogen orthophosphate (($Na_2PO_4$) and 0.01M ethylene diamine tetra acetic acid disodium salt (EDTA)], 0.1% SDS (Sodium dodecyl sulphate), 5× Denhardt's solution (0.1% Ficoll, 0.1% Polyvinyl pyrrolidone), and 0.2× BLOTTO (0.5% deratted milk power in water). After prehybridization, the solution was removed and was replaced by hybridization solution containing: 5× SSPE [0.75M Sodium chloride (NaCl), 0.05M Sodium dihydrogen orthophosphate (($Na_2PO_4$) and 0.01M ethylene diamine tetra acetic acid disodium salt (EDTA)], 0.1% SDS (Sodium dodecyl sulphate), 5× Denhardt's solution (0.1% Ficoll, 0.1% Polyvinyl pyrrolidone), 0.2× BLOTTO (0.5% defatted milk in water), 10% Dextral sulphate and the purified, labeled probe. Hybridization was carried out at 65° C. for one overnight with gentle shaking. After overnight hybridization, probe was discarded and filters were initially washed thrice for 30 min each at room temperature with a solution containing 2× SSPE [0.3M Sodium chloride (NaCl), 0.02M Sodium dihydrogen orthophosphate (($Na_2PO_4$) and 0.004M ethylene diamine tetra acetic acid disodium salt (EDTA)], 0.1% SDS with gentle shaking. Hot wash was given at 65° C. with a solution containing 2× SSC, 0.1% SDS for 10 minutes. The filter was transferred to a filter paper to remove excess of liquid, covered in thin plastic sheet and exposed to X-ray films for 4 days at −70° C. using intensifying screens.

The gel blot analysis revealed hybridization of the labeled semisynthetic amplicon, specifically to male papaya DNA in all the three different cultivars tested.

Advantages of the Present Invention

1. The important advantage is to provide a semisynthetic amplicon useful for sex determination of dioecious papaya plant.
2. The present invention will be highly useful in intra and interspectific breeding experiments and for screening the F1 and F2 generations for male and female plants.
3. With this invention, the sex of the papaya plants can be identified before flowering, allowing direct transplantation and distribution of only the identified female plants.
4. The said process is fast, accurate, does not involve hazardous chemicals.
5. The genotype of the plant is not affected in the process of identification of sex of the plant
6. The said process requires minimal amount of sample material.
7. The process is very much cost effective and a large number of samples can be processed in a very short duration.

8. Environmental and seasonal variations do not interfere in the process of preparation of semisynthetic amplicon.

We claim:

1. A DNA fragment comprising 831 bp having the nucleotide sequence:

gaggatccct attagtgtaa gggatgt-
tca agaacctagc tctgatatca cctatgacat ctcggtaccg aat-
agggcaa cggtgtctga caacataata gatatgagtg cataaaagaa ctatacaa-
ca gaagaaaagt catttcttat aaaaatttga tgtttaaata-
catttgagat caagaacttg gtagttaaaa tatatacaag cattattata tcaacttc-
ta tattacaaaa taattgttta tcagagtaca ataattcaca tgcact-
taaa ttacgctaca agttcacgaa caaatccaaa caaactttaa tggtg-
cagtt tgagcagcag caatcttcac -continued

```
tttcgtatct ctaggggaaa tagagt-
tggg gtgactttca taagactcag taaactctgt acggaaaata gtatt-
taaaa tacggtaata aaggtttaaa ggttgtttat tttaaaaatg tgtcatac-
ct tttcattcaa tagagcttac cgtcagagtc cgttgcagat taaat-
tcatt taaaatacta ctaaaaagtt catacttttg gttaattgaa atacattt-
ta aaataccaaa atttcaaaca taagcagtaa aactgaatga gaaa-
catatt tggaaccagt ggaattatct aaacatagaa agacgagaca gagtagt-
gag aaacatagca aactcaacat gcggtcaaaa tcatagaaat aaatcaat-
ag tcctagctag caattaaact atttggttca attacagtgt tttaca-
gatc ttcacacaaa gccattttaa cttatatcag cagagtgcaa aagggatcct c (SEQ ID NO:1).
```

2. A method of determining the sex of a dioecious papaya plant comprising:
  (a) providing the DNA fragment of claim 1 or a strand fully complementary thereto;
  (b) determining whether said fragment or complementary strand hybridizes to a DNA sample from a papaya plant, wherein hybridization is indicative that the papaya plant is male.

3. The DNA fragment of claim 1 or a strand fully complementary thereto, wherein said DNA fragment is labelled.

4. A process for sex determination of dioecious papaya plants, said process comprising isolating the DNA from any part of a papaya plant, amplifying said DNA in a Random Amplification of Polymorphic DNA Polymerase Chain Reaction (RAPD-PCR), resolving the amplified products by gel electrophoresis, detecting the amplified resolved products, identifying a sex specific, double stranded amplified resolved product, eluting the said sex specific product from the gel, cloning said eluted product in a vector, and sequencing said cloned product, wherein the presence of the sequence as defined in claim 1 is indicative that the sex of the papaya plant is male.

5. A process as claimed in claim 4 wherein, the polymerase chain reactions are carried out using a thermostable DNA polymerase enzyme.

6. A process as claimed in claim 4, wherein the Random Amplification of Polymorphic DNA Polymerase Chain Reaction (RAPD-PCR) is effected using one or more single stranded oligonucleotide primers.

7. A process as claimed in claim 4, wherein resolution of the products of polymerase chain reaction is effected by electrophoresis using agarose gel, polyacrylamide gel or mixtures thereof.

8. A process as claimed in claim 4, wherein detection of amplified resolved products is effected by ethidium bromide staining or autoradiography.

9. A process as claimed in claim 4, wherein identification of the sex specific double stranded product is effected by comparing the amplification products of RAPD-PCR of different sex forms of papaya.

10. A process as claimed in claim 4, wherein elution of the sex specific product from the gel is effected by electroelution or a freeze-thaw method.

11. A process as claimed in claim 4, wherein cloning of the eluted product is effected using a plasmid vector.

12. A process as claimed in claim 4 wherein, sequencing of the cloned product is effected by Sanger's dideoxy method.

13. A process for preparing a sex-specific semisynthetic amplicon, useful for sex determination of dioecious papaya plants, which comprises,
  synthesizing a pair of single stranded oligonucleotides by a known method said pair of single stranded oligonucleotides consisting of an oligonucleotide comprising SEQ ID NO: 2, and an oligonucleotide comprising SEQ ID NO: 3 ,and
  amplifying genomic DNA of a papaya plant in a conventional Sequence Tagged Site Polymerase Chain Reaction using the pair of oligonucleotides as primers to obtain the sex specific semisynthetic amplicon.

14. A process as claimed in claim 13, wherein Sequence Tagged Site Polymerase Chain Reaction is effected using a pair of oligonucleotide primers consisting of SEQ ID NO: 2 and SEQ ID NO: 3.

* * * * *